(12) United States Patent
Chou

(10) Patent No.: US 8,347,885 B2
(45) Date of Patent: Jan. 8, 2013

(54) NASAL FILTER

(76) Inventor: Chun-Yu Chou, Taipei (TW)

(*) Notice: Subject to any disclaimer, the term of this patent is extended or adjusted under 35 U.S.C. 154(b) by 246 days.

(21) Appl. No.: 12/950,132

(22) Filed: Nov. 19, 2010

(65) Prior Publication Data
US 2012/0125340 A1 May 24, 2012

(51) Int. Cl.
A61G 10/00 (2006.01)
A61M 16/00 (2006.01)

(52) U.S. Cl. .................................. 128/206.11

(58) Field of Classification Search ............ 128/200.24, 128/204.11, 204.12, 205.27, 205.29, 206.11, 128/207.13; 606/199
See application file for complete search history.

(56) References Cited

U.S. PATENT DOCUMENTS

| | | | | |
|---|---|---|---|---|
| 1,443,820 A * | 1/1923 | Hudson | ............... | 128/202.13 |
| 2,427,721 A * | 9/1947 | Goldstein | ............... | 128/203.22 |
| 3,457,917 A * | 7/1969 | Mercurio | ............... | 128/204.12 |
| 4,267,831 A * | 5/1981 | Aguilar | ............... | 128/203.14 |
| 5,417,205 A * | 5/1995 | Wang | ............... | 128/206.11 |
| 5,425,359 A * | 6/1995 | Liou | ............... | 128/206.11 |
| 6,561,188 B1 * | 5/2003 | Ellis | ............... | 128/206.11 |
| 2003/0106555 A1 * | 6/2003 | Tovey | ............... | 128/205.27 |
| 2003/0106556 A1 * | 6/2003 | Alperovich et al. | ..... | 128/206.11 |
| 2005/0211250 A1 * | 9/2005 | Dolezal et al. | ............ | 128/206.11 |
| 2007/0027542 A1 * | 2/2007 | Xu | ............... | 623/13.17 |
| 2010/0059060 A1 * | 3/2010 | Evensson | ............ | 128/205.27 |
| 2010/0147307 A1 * | 6/2010 | Narciso | ............ | 128/206.11 |

* cited by examiner

Primary Examiner — Kristen Matter
(74) Attorney, Agent, or Firm — Rosenberg, Klein & Lee

(57) ABSTRACT

A nasal filter includes a main body, a cover, and a filtering medium. The main body has a hollow cylinder, a boss connected to a spherical member, a flange, and a plurality of internal guide vanes. The hollow cylinder has a front and a rear opening. A first threaded portion is formed on the outer surface at the front end portion of the hollow cylinder. A thru hole is formed on the cover and aligns correspondingly to the front opening of the hollow cylinder. A second threaded portion is formed on the inner surface of the cover for mating to the first threaded portion on the hollow cylinder. The filtering medium is held in between the cover and the hollow cylinder and covers the thru hole. A filter pad is further included to provide additional functions. Accordingly, the nasal filter offers air purification and doe not cover the mouth.

5 Claims, 4 Drawing Sheets

NASAL FILTER

BACKGROUND OF THE INVENTION

1. Field of the Invention

The instant disclosure relates to a nasal filter; in particular, a nasal filter to fit inside the human nostrils.

2. Description of Related Art

Because of allergic rhinitis, or stuffy nose, the inventor has to wear a surgical mask regularly to keep out airborne irritants. The mask has elastic strings that hang around the ears of the user, and the mask would cover the user's nose and mouth.

The primary function of the mask is air filtering to keep irritants from entering the nose, because the irritants can cause irritation and inflammation to some internal areas of the nose. Since the filtering objective is mainly for the nose, only the nose area needs to be covered by the mask.

To meet the above objective, the inventor proposes the following solution.

SUMMARY OF THE INVENTION

The object of the instant disclosure is to provide a nasal filter to fit inside the human nostrils.

Structurally, the nasal filter comprises a main body having a hollow cylinder; a boss connected to the rear end portion of the hollow cylinder; a flange formed on the outer surface of the middle portion of the hollow cylinder; and a plurality of separate guide vanes arranged in intervals on the inner wall of the hollow cylinder. The hollow cylinder further comprises a front and a rear opening. A first threaded portion is formed on the outer surface of the front end portion of the hollow cylinder, and a spherical member is located at the top end of the boss. The nasal filter also includes a cover having a thru hole, which aligns correspondingly to the front opening of the hollow cylinder. A second threaded portion is formed on the inner surface of the cover, where the second threaded portion mates to the first threaded portion. A filtering medium is held in between the main body and the cover and covers the thru hole.

Functionally, the nasal filter has several advantages as follows. The nasal filter does not cover up the mouth, which allows the user to speak and dine without obstruction. Also, the nasal filter has a better air-tight seal, is less likely to slip off, moderates airflow, and has a filtering medium that can be replaced easily.

To further appreciate the characteristics and technical contents of the instant disclosure, references are hereunder made to the detailed descriptions and appended drawings in connection with the instant disclosure. However, the appended drawings are merely shown for exemplary purposes, rather than being used to restrict the scope of the instant disclosure.

DETAILED DESCRIPTION OF THE PREFERRED EMBODIMENT

Figure 1:
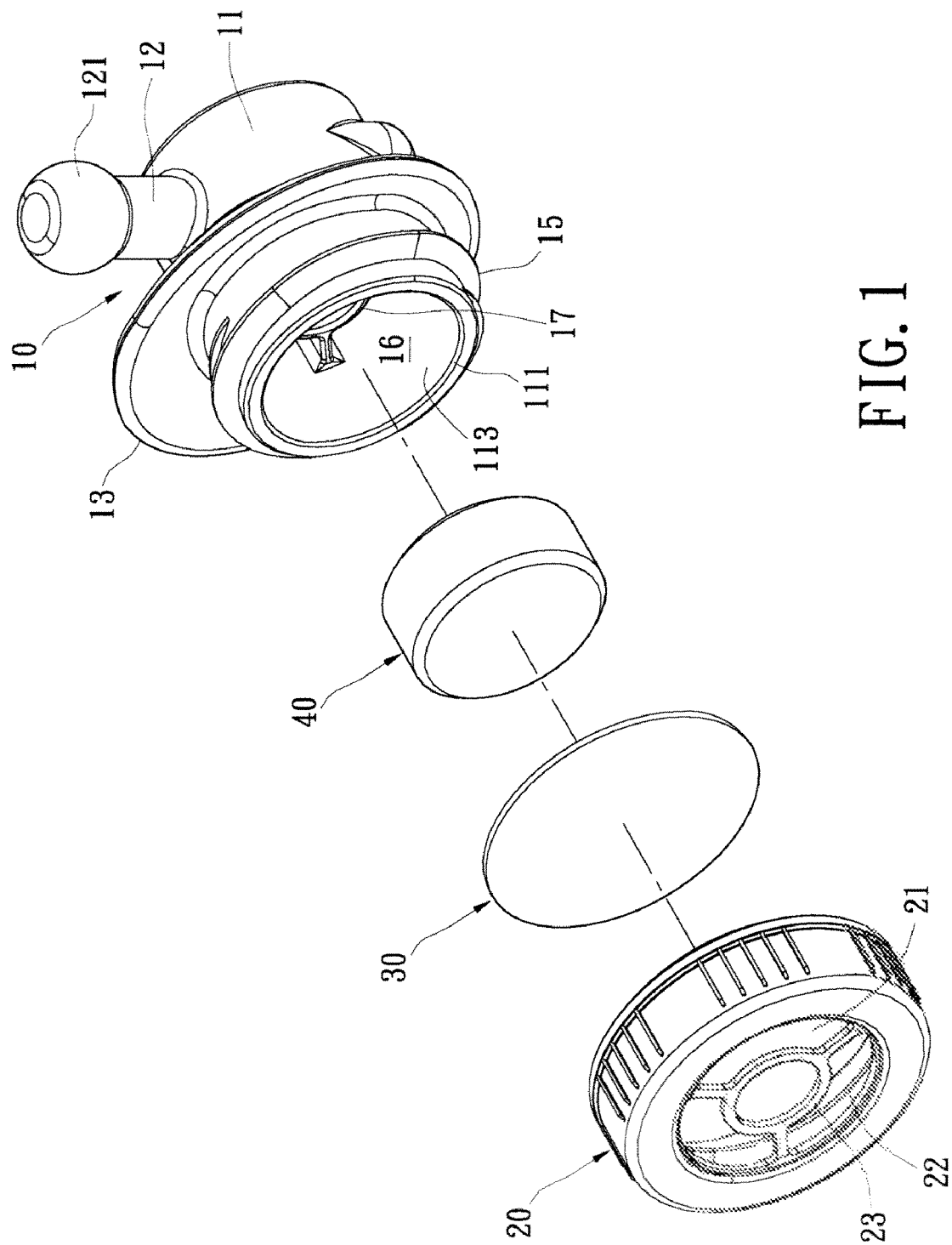
FIG. 1 is an exploded view of a nasal filter of the instant disclosure.
Figure 2:
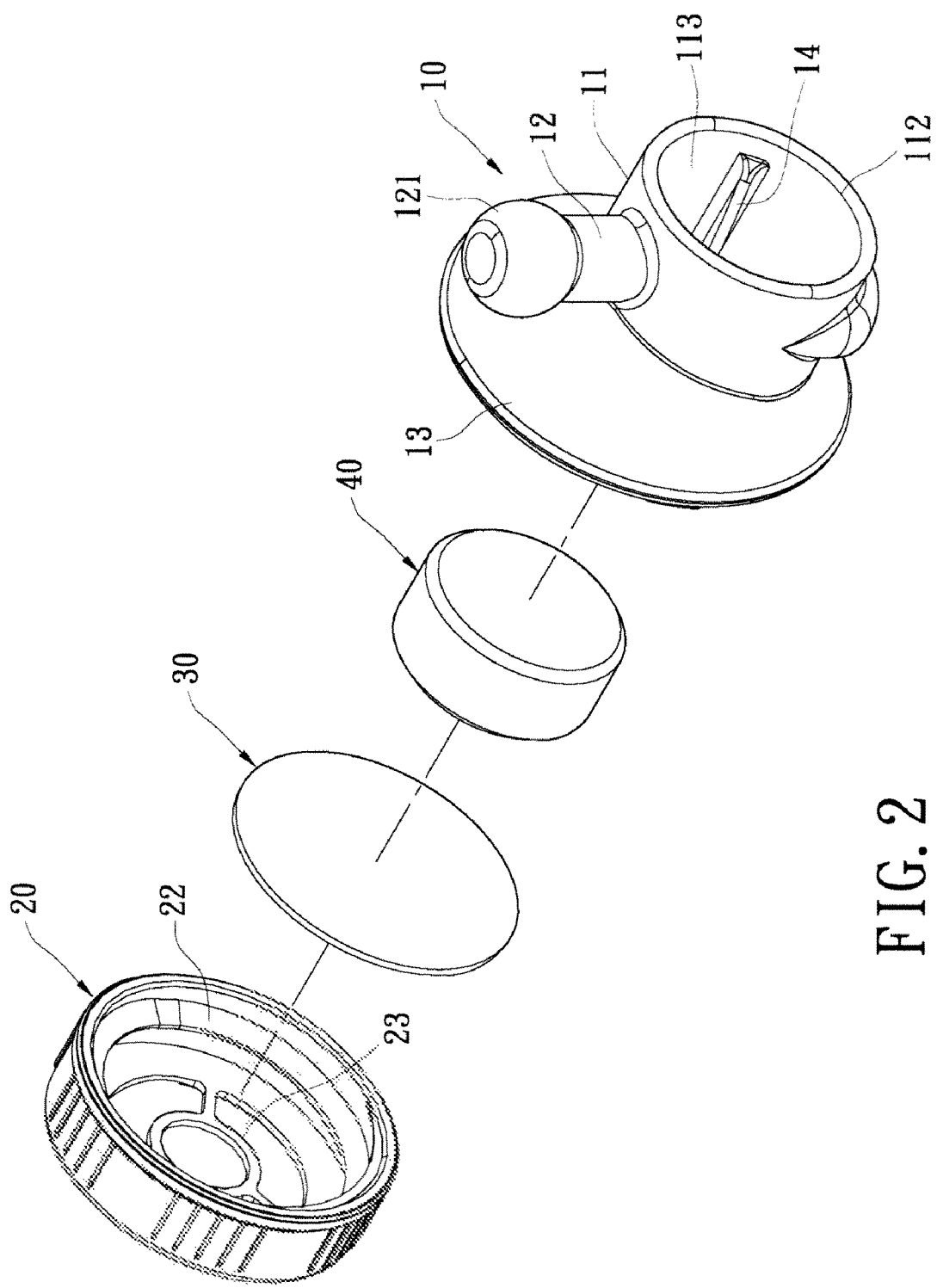
FIG. 2 is another exploded view of the nasal filter.

Please refer to FIGS. 1 and 2, which show a nasal filter of the instant disclosure having a main body 10, a cover 20, and a filtering medium 30. The main body 10 is made of medical-grade soft plastic material, in providing comfort when contact human skin. The main body 10 comprises a hollow cylinder 11, a boss 12, a flange 13, and a plurality of guide vanes 14. A front and rear opening 111 and 112 is formed at the front and rear end portion of the hollow cylinder 11 respectively. A first threaded portion 15 is formed on the outer surface at the front end of the hollow cylinder 11.

The boss 12 is connected to the rear end of the hollow cylinder 11, and a spherical member 121 is located at the top end of the boss 12. Based on ergonomics, the spherical member 121 is specifically designed for fitting inside the human nostrils.

The flange 13 is formed integrally off the outer surface of the middle portion of the hollow cylinder 11. In particular, the flange 13 slopes away from the boss 12.

Figure 3:
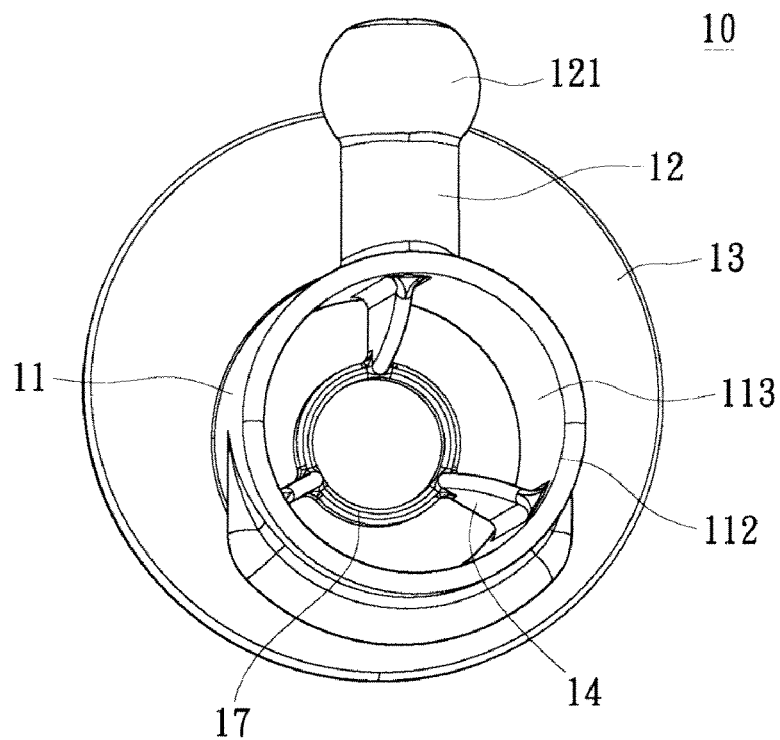
FIG. 3 is an isometric view of a main body of the nasal filter.

As shown in FIG. 3, the guide vanes 14 protrude off the inner wall 113 of the hollow cylinder 11 and are disposed in interval. In the exemplary embodiment, the number of guide vane is three and spaced 120 degrees apart from each other. However, the number of guide vane and the angle is not restricted.

A thru hole 21 is centrally formed on the cover 20 and aligns correspondingly to the front opening 111 of the hollow cylinder 11. A second threaded portion 22 is formed on the inner surface of the cover 20, for mating correspondingly to the first threaded portion 15 on the main body 10. The cover 20 further has a grid 23 disposed in the thru hole 21, to prevent the filtering medium 30 from slipping off the cover 20.

The disposable filtering medium 30 has a round shape with a small surface area. However, the filtering medium 30 has full filtering capability, with the filtering material can be activated carbon or specific germ-killing filter membrane.

The above features make up the nasal filter of the instant disclosure, while the assembled nasal filter will be discussed as follows.

Figure 4:
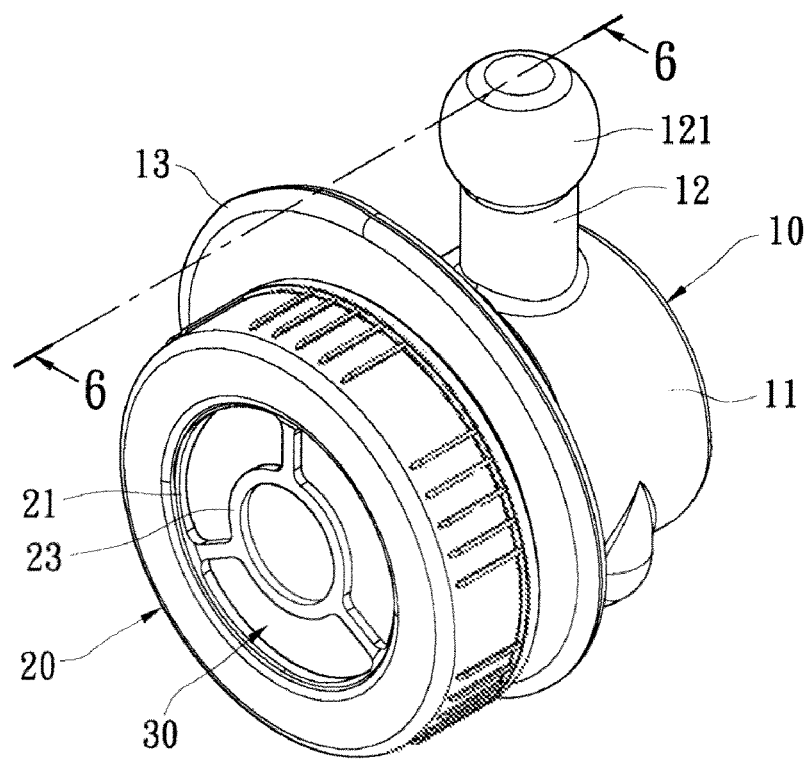
FIG. 4 is an isometric view of the assembled nasal filter.
Figure 5:
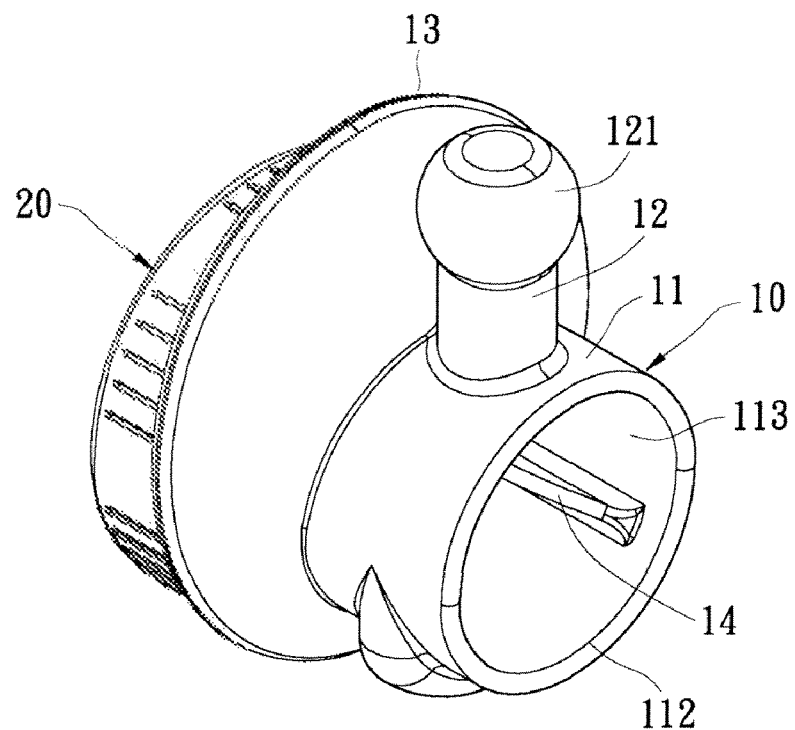
FIG. 5 is another isometric view of the assembled nasal filter.
Figure 6:
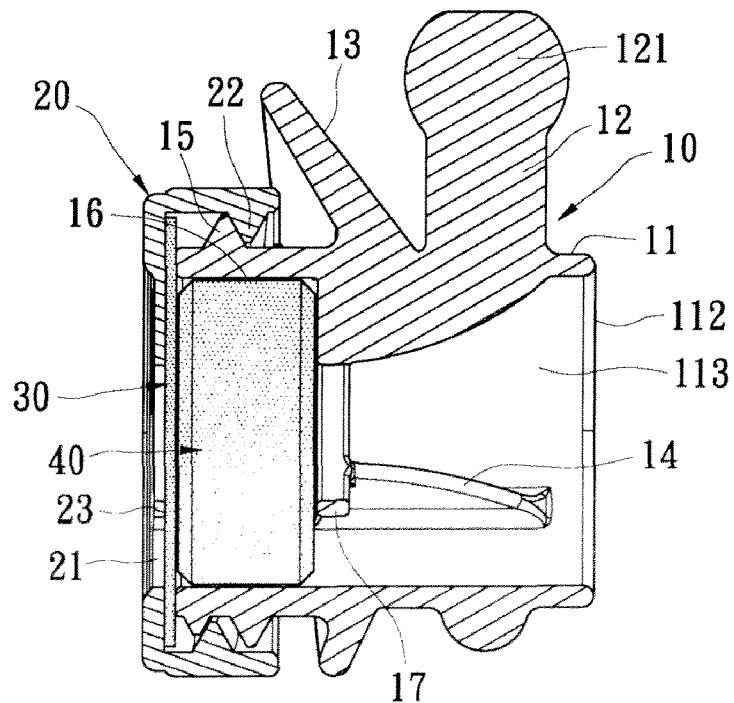
FIG. 6 is a cross-sectional view of the nasal filter of FIG. 4.

Please refer to FIGS. 4-6, which show the assembled nasal filter of the instant disclosure. The second threaded portion 22 of the cover is screwed onto the first threaded portion 15 of the main body 10. Thereby, the cover 20 is tightly secured onto the front end of the main body 10, which also results the filtering medium 30 being anchored in between the main body 10 and the cover 20. In doing so, the filtering medium 30 covers the thru hole 21 of the cover 20 to filter the incoming air. To replace the filtering medium 30, just unscrew the cover 20 off the main body 10 to expose the filtering medium 30. The replacement process is easy and efficient.

To wear the nasal filter, each human nostril is inserted with one nasal filter. Namely, the rear portion of the main body 10 behind the flange 13, or the portion of the main body 10 with the rear opening 112, is inserted into the human nostril. Meanwhile, the sloped surface of the flange 13 gently contours around the tip of the nostril to provide a snug seal. In other words, the front portion before the flange 13, such as the cover 20, is exposed outside of the nostril. The spherical member 121 fits firmly inside the nostril, thus preventing from slipping off accidentally.

Therefore, when the wearer breathes, air enters through the thru hole 21 and passes through the filtering medium 30. The filtering medium 30 traps the dust particles and allows purified air to enter the nose cavity via the rear opening 112. In addition, the guide vanes 14 act as whiskers to moderate the air flow.

As a safety feature, a ring portion 17 is formed inside the hollow cylinder 11 as shown in FIGS. 1, 3, and 6. The guide vanes 14 are connected in between the ring portion 17 and the inner wall 113 of the hollow cylinder 11. When the wearer breathes too hard, the ring portion 17 blocks the filtering medium 30 from being suctioned into the nose cavity.

In addition, a receiving space 16 is defined by the inner wall 113 and the ring portion 17. The receiving space 16 is located in front of the guide vanes 14 for inserting a filter pad 40. Based on need, the filter pad 40 can be any specific type, such as for retaining pollen, cold air relief, high efficiency, freshener, or supplies medicine through the nasal cavity by inhaling. Therefore, the filter pad 40 provides added function to the nasal filter in addition to air purification.

As briefly mentioned in the previous section, the advantages with the nasal filter of the instant disclosure are explained in details as follows. The nasal filter is designed to be inserted into the human nostrils. Unlike conventional mouth mask, the nasal filter does not cover the mouth, which allows the user to speak and dine freely without obstruction. The nasal filter can be quickly inserted or removed easily. Also, the sloped surface of the flange provides a snug seal to the tip of the nose, thus providing both comfort and good sealing effect. The boss and the spherical member allow the nasal filter to fit securely in the nostril in preventing slipping off accidentally. Meanwhile, the guide vanes moderate the airflow into the nose in providing better comfort to the user. To replace the filtering medium, the cover can be screwed on and off the main body easily for easy access.

The descriptions illustrated supra set forth simply the preferred embodiment of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. A nasal filter, comprising:
   a main body having a hollow cylinder, the hollow cylinder having a front opening and a rear opening, a boss connected to a rear end portion of the hollow cylinder, a spherical member connected to a top end of the boss for insertion into a nostril of a user, a flange formed on an outer surface of the hollow cylinder, a plurality of guide vanes arranged in intervals on an inner wall of the hollow cylinder, and a first threaded portion formed on the outer surface at a front end portion of the hollow cylinder;
   a cover having a thru hole aligned with the front opening of the hollow cylinder and a second threaded portion formed on an inner wall of the cover for mating to the first threaded portion of the main body; and
   a filtering medium disposed in between the cover and the main body that covers the thru hole.

2. The nasal filter of claim 1, wherein the hollow cylinder has an internal ring portion and the guide vanes are connected in between the ring portion of the inner wall of the hollow cylinder.

3. The nasal filter of claim 2, wherein a receiving space is formed by the inner wall of the hollow cylinder and the ring portion, the receiving space is located in front of the guide vanes for holding a filter pad.

4. The nasal filter of claim 1, wherein the flange slopes away from the boss.

5. The nasal filter of claim 1, wherein a grid is formed on the cover at the thru hole.

* * * * *